United States Patent
Gillespie et al.

(10) Patent No.: US 11,051,853 B2
(45) Date of Patent: *Jul. 6, 2021

(54) SYSTEMS AND METHODS FOR PERCUTANEOUS REMOVAL OF OBJECTS FROM AN INTERNAL BODY SPACE

(71) Applicants: THE TRUSTEES OF THE UNIVERSITY OF PENNSYLVANIA, Philadelphia, PA (US); THE CHILDREN'S HOSPITAL OF PHILADELPHIA, Philadelphia, PA (US)

(72) Inventors: Matthew J. Gillespie, Bryn Mawr, PA (US); Mark Piper, West Chester, PA (US); Joseph H. Gorman, III, Lower Gwynedd, PA (US); Robert C. Gorman, Lower Gwynedd, PA (US)

(73) Assignees: The Trustees of the University of Pennsylvania, Philadelphia, PA (US); The Children's Hospital of Philadelphia, Philadelphia, PA (US)

(*) Notice: Subject to any disclaimer, the term of this patent is extended or adjusted under 35 U.S.C. 154(b) by 193 days.

This patent is subject to a terminal disclaimer.

(21) Appl. No.: 15/757,144

(22) PCT Filed: Sep. 2, 2016

(86) PCT No.: PCT/US2016/050108
§ 371 (c)(1),
(2) Date: Mar. 2, 2018

(87) PCT Pub. No.: WO2017/040926
PCT Pub. Date: Mar. 9, 2017

(65) Prior Publication Data
US 2018/0271685 A1    Sep. 27, 2018

Related U.S. Application Data

(60) Provisional application No. 62/214,475, filed on Sep. 4, 2015.

(51) Int. Cl.
A61B 17/50    (2006.01)
A61B 17/221   (2006.01)
(Continued)

(52) U.S. Cl.
CPC ............ *A61B 17/50* (2013.01); *A61B 17/221* (2013.01); *A61B 17/22031* (2013.01);
(Continued)

(58) Field of Classification Search
CPC . A61B 17/22031; A61B 17/221; A61B 17/50; A61B 2017/00367;
(Continued)

(56) References Cited

U.S. PATENT DOCUMENTS 5,064,428 A   11/1991   Cope et al.
5,102,415 A    4/1992   Guenther et al.
(Continued)

FOREIGN PATENT DOCUMENTS

WO    00/53120 A1    9/2000
WO    2015/031898 A2    3/2015

*Primary Examiner* — Jocelin C Tanner
(74) *Attorney, Agent, or Firm* — BakerHostetler

(57) ABSTRACT

Disclosed are systems, methods, and devices for percutaneous retrieval of objects, such as endovascular devices, from a subject's internal body space. The present inventions have vascular, non-vascular (gastrointestinal), and surgical (laproscopic) applications. The inventions include the use of a retrieval end having one or more compressed states and an expanded state, the retrieval end adopting the expanded state when the retrieval end is deployed into a subject's internal body space, the retrieval end having a mouth through which an object can be passed into an interior space within the retrieval end when the retrieval end is in the expanded state, the mouth being adjustable between an opened state and a
(Continued)

closed state so that the object can be enclosed within the interior space after passing through the mouth of the retrieval end.

32 Claims, 6 Drawing Sheets

(51) Int. Cl.
    *A61B 17/22*     (2006.01)
    *A61F 2/962*     (2013.01)
    *A61F 2/24*     (2006.01)
    *A61B 17/00*     (2006.01)
    *A61F 2/95*     (2013.01)

(52) U.S. Cl.
    CPC .... *A61F 2/962* (2013.01); *A61B 2017/00367* (2013.01); *A61B 2017/00778* (2013.01); *A61B 2017/2215* (2013.01); *A61B 2017/22034* (2013.01); *A61B 2017/22035* (2013.01); *A61F 2/2427* (2013.01); *A61F 2002/9528* (2013.01)

(58) Field of Classification Search
    CPC .......... A61B 2017/00778; A61B 2017/22034; A61B 2017/22035; A61B 2017/2215; A61F 2/2427; A61F 2/962; A61F 2002/9528
    See application file for complete search history.

(56) References Cited

U.S. PATENT DOCUMENTS

| | | |
|---|---|---|
| 5,972,019 A | 10/1999 | Engelson et al. |
| 6,190,394 B1 | 2/2001 | Lind et al. |
| 6,383,195 B1 * | 5/2002 | Richard ............... A61B 17/221 606/114 |
| 6,569,181 B1 | 5/2003 | Burns |
| 6,632,236 B2 | 10/2003 | Hogendijk |
| 6,878,151 B2 | 4/2005 | Carrison et al. |
| 6,893,450 B2 | 5/2005 | Foster |
| 7,004,954 B1 | 2/2006 | Voss et al. |
| 7,063,707 B2 | 6/2006 | Bose et al. |
| 7,101,380 B2 | 9/2006 | Khachin et al. |
| 7,727,243 B2 | 6/2010 | Sepetka et al. |
| 7,998,163 B2 | 8/2011 | Salahieh et al. |
| 8,038,704 B2 | 10/2011 | Sherburne |
| 8,167,903 B2 | 5/2012 | Hardert et al. |
| 8,298,252 B2 | 10/2012 | Krolik et al. |
| 8,795,305 B2 | 8/2014 | Martin et al. |
| 8,801,748 B2 | 8/2014 | Martin |
| 8,858,497 B2 | 10/2014 | Di et al. |
| 8,858,567 B2 | 10/2014 | Saleh |
| 8,870,895 B2 | 10/2014 | Bilitz |
| 9,005,237 B2 | 4/2015 | Eckhouse et al. |
| 9,055,963 B2 | 6/2015 | Miloslavski et al. |
| 9,149,609 B2 | 10/2015 | Ansel et al. |
| 9,220,522 B2 | 12/2015 | Fulkerson et al. |
| 9,265,914 B2 | 2/2016 | Fulton et al. |
| 9,398,945 B2 | 7/2016 | Groff |
| 9,427,252 B2 | 8/2016 | Sos |
| 9,445,829 B2 | 9/2016 | Brady et al. |
| 9,480,491 B1 | 11/2016 | Dostal et al. |
| 10,092,324 B2 * | 10/2018 | Gillespie ............... A61B 17/221 |
| 2001/0041909 A1 | 11/2001 | Tsugita et al. |
| 2004/0010280 A1 * | 1/2004 | Adams .................... A61F 2/013 606/194 |
| 2004/0260333 A1 | 12/2004 | Dubrul et al. |
| 2006/0047286 A1 | 3/2006 | West |
| 2006/0047586 A1 | 3/2006 | Wolf |
| 2006/0195118 A1 * | 8/2006 | Richardson .......... A61B 17/221 606/113 |
| 2007/0208367 A1 | 9/2007 | Fiorella et al. |
| 2007/0213749 A1 | 9/2007 | Kogasaka et al. |
| 2009/0195118 A1 | 8/2009 | An |
| 2009/0292307 A1 | 11/2009 | Razack |
| 2010/0152609 A1 | 6/2010 | Zwolinski et al. |
| 2011/0046655 A1 | 2/2011 | Arnott et al. |
| 2011/0230955 A1 * | 9/2011 | Orion ....................... A61F 2/82 623/1.15 |
| 2012/0059309 A1 * | 3/2012 | di Palma ................ A61B 17/22 604/22 |
| 2012/0289971 A1 * | 11/2012 | Segermark ........... A61B 17/221 606/108 |
| 2013/0018387 A1 | 1/2013 | Diamant |
| 2013/0178888 A1 * | 7/2013 | Bliss .................... A61B 17/221 606/200 |
| 2013/0261638 A1 | 10/2013 | Diamant et al. |
| 2014/0172008 A1 | 6/2014 | McKinnis et al. |
| 2014/0277086 A1 | 9/2014 | Hagan |
| 2014/0277099 A1 | 9/2014 | Wallace et al. |
| 2014/0303667 A1 | 10/2014 | Cox et al. |
| 2015/0105819 A1 | 4/2015 | Becking et al. |
| 2015/0173783 A1 | 6/2015 | Tah et al. |
| 2015/0238207 A1 * | 8/2015 | Cox ....................... A61B 17/221 606/159 |
| 2015/0250578 A1 | 9/2015 | Cook et al. |
| 2015/0305757 A1 * | 10/2015 | Brayman ............... A61B 17/221 606/128 |
| 2016/0015403 A1 | 1/2016 | Nguyen et al. |
| 2016/0022293 A1 | 1/2016 | Dubrul et al. |
| 2016/0095690 A1 | 4/2016 | Becking et al. |
| 2016/0206426 A1 | 7/2016 | Khoynezhad et al. |
| 2016/0374702 A1 | 12/2016 | St et al. |

\* cited by examiner

SYSTEMS AND METHODS FOR PERCUTANEOUS REMOVAL OF OBJECTS FROM AN INTERNAL BODY SPACE

CROSS-REFERENCE TO RELATED APPLICATIONS

This application is the National Stage Application of International Patent Application No. PCT/US2016/050108, filed Sep. 2, 2016 which claims priority to U.S. Provisional Patent Application No. 62/214,475, filed Sep. 4, 2015, the entire contents of both of which are incorporated herein by reference.

TECHNICAL FIELD

The present disclosure pertains to noninvasive removal of objects, including endovascular devices such as stents or valve prostheses, from a subject's body.

BACKGROUND

Since the advent of stents and stent grafts were conceived in the 1980's by Drs. Julio Palmaz and Juan Parodi and popularized in the 1990's, the interventional cardiovascular market has grown to a multi-billion dollar enterprise worldwide. A variety of stent-like devices leveraging the techniques of stent delivery and implantation have been in continuous state of development ever since. In the early 2000's, Professor Alain Cribier performed the first catheter-based valve replacement in France. An intensive development of transcatheter aortic valve replacement (TAVR) by more than 30 companies has since led the industry to a revolutionary procedure that treats fully ⅓ of patients with stenotic and/or regurgative aortic valve disease who are not surgical candidates and previously could not be treated. This development effort has paved the way for a far larger patient population who are contraindicated for surgery with mitral valve regurgitation. These newly developed and developing valve replacement procedures are complex and varied in delivery methodology however, and can be prone to misplacement or dislodgement of the implants, particularly in a physician's early learning phases, but even by highly trained and seasoned operators. Currently, there is no existing catheter based technology to rescue an interventionist in these cases.

Percutaneous heart and vascular therapies continue to expand. As technology advances, endovascular devices will only continue to increase in size and complexity. Current endovascular devices include, for example, heart valves, vascular stents, aortic aneurysm grafts, vascular closure devices (such as atrial or ventricular septal closure devices), vena caval filters, pacemaker leads, atrial appendage occluders, vascular plugs, vascular coils, aneurysm excluders, dialysis catheters, and the like. Most of these devices are designed to have a low profile for passage through a catheter prior to expanding to their larger, functional state once introduced into the vasculature. Precise placement of these devices is necessary for proper function.

However, even in the most skilled hands, device malposition can occur, which can result in significant complications, and that conventionally require emergency surgery for device removal. A retrieval system that permits the percutaneous capture and removal of endovascular devices, including comparatively large ones, would make these percutaneous procedures safer, for example, by providing a "bail out" option for procedures gone awry.

SUMMARY

The present disclosure provides systems for percutaneous retrieval of an object, such as an endovascular device, the systems comprising an outer sheath having a lumen and being adapted for insertion into a subject's internal body space; an inner sheath that is adapted for insertion into the subject's internal space via the lumen of the outer sheath, the inner sheath comprising a distal retrieval end having one or more compressed states and an expanded state, the retrieval end adopting one of the compressed state when the retrieval end is housed within the lumen of the outer sheath, and adopting the expanded state when the retrieval end is deployed into the subject's internal body space by exiting a distal end of the outer sheath, the retrieval end having a mouth through which the object can be passed into an interior space within the retrieval end when the retrieval end is in the expanded state, the mouth being adjustable between an opened state and a closed state so that the object can be enclosed within the interior space after passing through the mouth of the retrieval end; wherein when at least a portion of the retrieval end of the inner sheath is withdrawn into the outer sheath following capture of the object within the interior space of the retrieval end, the retrieval end exerts an inward force that at least partially collapses or compresses the object.

Also disclosed are methods for percutaneously retrieving an object, such as an endovascular device, within a subject's internal body space, the methods comprising: delivering to the subject's internal body space outer sheath having a lumen; introducing an inner sheath into the lumen of the outer sheath, the inner sheath comprising a distal retrieval end having one or more compressed states and an expanded state, the retrieval end adopting one of the compressed states when the retrieval end is housed within the lumen of the outer sheath, and adopting the expanded state when the retrieval end is deployed into the subject's internal body space by exiting a distal end of the outer sheath, the retrieval end having a mouth through which the object can be passed into an interior space within the retrieval end when the retrieval end is in the expanded state, the mouth being adjustable between an opened state and a closed state so that the object can be enclosed within the interior space after passing through the mouth of the retrieval end; advancing the inner sheath through the lumen of the outer sheath until the retrieval end is deployed into the subject's internal body space by exiting the distal end of the outer sheath; capturing the object at least partially within the interior space of the retrieval end; at least partially closing the mouth of the retrieval end in order to enclose the object within the interior space of the retrieval end; withdrawing the inner sheath through the lumen of the outer sheath until the retrieval end exerts an inward force that at least partially collapses or compresses the object; and, withdrawing the retrieval end into the lumen of the outer sheath, thereby removing the object from the subject's internal body space.

The present disclosure also pertains to devices for percutaneously retrieving an object, such as an endovascular device, from a subject's internal body space, the devices comprising: an elongated tube portion that terminates in a distal retrieval end, the distal retrieval end comprising a wire weave and having one or more compressed states and an expanded state, the retrieval end adopting one of the compressed states when the retrieval end is housed within the lumen of an outer sheath, and adopting the expanded state when the retrieval end is deployed into the subject's internal body space by exiting a distal end of the outer sheath, the retrieval end having a mouth through which the object can be passed into an interior space within the retrieval end when the retrieval end is in the expanded state, the mouth being adjustable between an opened state and a closed state so that the object can be enclosed within the interior space after passing through the mouth of the retrieval end.

BRIEF DESCRIPTION OF THE DRAWINGS

These and other advantages of the percutaneous retrieval device of the invention will be apparent from the following detailed description in conjunction with the accompanying drawings, of which.

DETAILED DESCRIPTION OF ILLUSTRATIVE EMBODIMENTS

Figure 1:
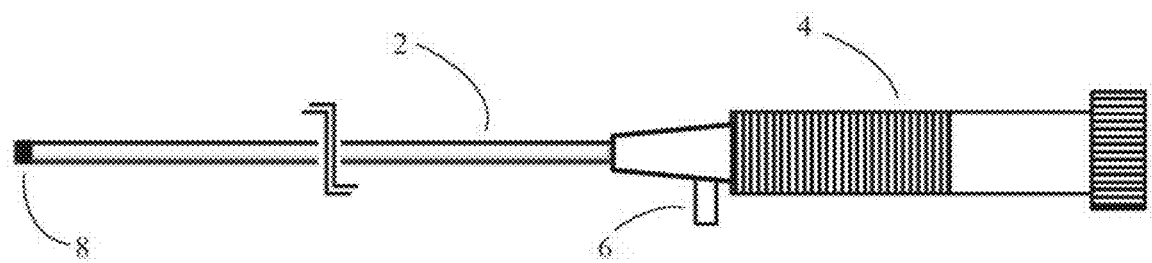
FIG. 1 is an illustration of an exemplary outer sheath according to the present systems.

The present inventions may be understood more readily by reference to the following detailed description taken in connection with the accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a particle" is a reference to one or more of such particles and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

The present disclosure relates, inter alia, to systems, methods, and devices for percutaneous retrieval of objects, such as endovascular devices, from a subject's internal body space. The present inventions have vascular, non-vascular (gastrointestinal), and surgical (laproscopic) applications. For example, endovascular, endoscopic, and laporscopic uses are contemplated herein. As noted above, newly developed and developing valve replacement procedures are complex and varied in delivery methodology however, and can be prone to misplacement, even among highly experienced operators. Other devices and components thereof are likewise prone to being improperly positioned or being becoming displaced from the proper anatomical position. The presently disclosed systems and methods can be used to capture and remove heart valves, vascular stents, aortic aneurysm grafts, vascular closure devices (such as atrial or ventricular septal closure devices), vena caval filters, pacemaker leads, atrial appendage occluders, vascular plugs, vascular coils, aneurysm excluders, dialysis catheters, other embolized foreign bodies, and the like. Even bodies that are not of foreign origin, such as large, organized thrombi, can be removed by the present systems and methods. Any unwanted object within a subject's internal body space may be captured and removed in accordance with the present invention.

Even if an object of any of the above-noted types is properly positioned, there may arise a need to remove such a device at some point in time after implantation or introduction. For example, the patient's anatomy could be reacting adversely to the device, a different device or a more advanced version of the device is prescribed, the device is no longer need due to improved prognosis, or any other reason could apply that justifies removal of the object. Prior to the present invention, there was no catheter-based technology for capturing and removing an interventionist in any of these cases. The present invention not only creates a "bailout" procedure for TAVR, TMVR, and other endovascular placed devices, but it also provides an important level of security for hospitals and physicians entering into complex and risky procedures. Furthermore, unlike the present invention, prior systems for the removal of devices or other objects were capable of grasping the device to be removed, but were unable to compress them. The present systems capture, enclose, compress, and, to the extent possible based on the nature of the captured object, at least partially collapse or compress objects, such as endovascular devices. These and other benefits and unique features are described more fully herein.

Disclosed herein are systems for percutaneous retrieval of an object, such as an endovascular device, the systems comprising an outer sheath having a lumen and being adapted for insertion into a subject's internal body space; an inner sheath that is adapted for insertion into the subject's internal body space via the lumen of the outer sheath, the inner sheath comprising a distal retrieval end having one or more compressed states and an expanded state, the retrieval end adopting one of the compressed state when the retrieval end is housed within the lumen of the outer sheath, and adopting the expanded state when the retrieval end is deployed into the subject's internal body space by exiting a distal end of the outer sheath, the retrieval end having a mouth through which the object can be passed into an interior space within the retrieval end when the retrieval end is in the expanded state, the mouth being adjustable between an opened state and a closed state so that the object can be enclosed within the interior space after passing through the mouth of the retrieval end; wherein when at least a portion of the retrieval end of the inner sheath is withdrawn into the outer sheath following capture of the object within the interior space of the retrieval end, the retrieval end exerts an inward force that at least partially collapses or compresses the object.

The outer sheath may formed from an material that is medically compatible with accessing a human subject's internal body space, and that is capable of accommodating within a lumen the inner sheath and the retrieval end. The latter characteristic means, for example, that the outer sheath must be able to withstand the outward radial force exerted by the retrieval end in any of its compressed states, including both before the retrieval end has been deployed into the subject's internal body space, and after the retrieval and has captured and contains the object and has been withdrawn back into the lumen of the outer sheath. The outer sheath must also be able to withstand any forces that are applied against it as a result of the transition of the retrieval end of the inner sheath from a compressed to the expanded state, and also from the expanded state to a compressed state (such as after the retrieval end has captured an object). The outer sheath may be formed from a singular material such as a polymer or metal, or from a composite of materials. An examplary composite is formed from a biocompatible, polymeric material with a metalic reinforcement such as a radial wire wind or a braid. The outer sheath tube may also include an inner liner for lubricity.

Likewise, the geometric dimensions of the outer sheath must be compatible with accessing the subject's internal body space without causing damage thereto, and with accommodating within a lumen the inner sheath and the retrieval end. Thus, the outer diameter and length of the outer sheath must be compatible with a human subject's physiology and adequate for reaching the desired space within a subject's internal body space (such as a chamber of the heart, the gastrointestinal tract, and the like), and the inner diameter (defining the lumen) must be capable of accommodating the inner sheath and retrieval end. Exemplary lengths are about 27 to about 35 inches, about 29 to about 33 inches, about 30 to about 32 inches, or about 27 inches, about 28 inches, about 29 inches, about 30 inches, about 31 inches, about 32 inches, about 33 inches, about 34 inches, or about 35 inches. The outer diameter of the outer sheath may be from 9 to 43 French. The inner diameter of the outer sheath may be from 6 to 40 French. Correspondingly, the outer diameter of the inner sheath may be from 4 to 38 French.

The end of the outer sheath that is opposite that which is introduced into a subject may comprise a hemostasis valve and handle that may include a flushing luer. FIG. 1 is an illustration of an exemplary outer sheath 2 that includes a modified hemostasis valve and handle 4 with a flushing luer 6. Outer sheath 2 may also include a marker band 8 comprising tungsten, gold, platinum, or any other radioopaque material that is visible under fluoroscopy in order to assist with guidance and placement of the outer sheath within the subject's internal body space. The length of the outer sheath is the length necessary for the distal end to access a desired part of a subject's internal body space while the proximal end, i.e., the end remaining outside of the subject and optionally mated to a hemostasis valve and handle, is available for operator control. For example, the length of the outer sheath plus the hemostasis valve and handle may be about 25 to about 35 inches, for example, about 32 inches.

If a transapical percutaneous approach is used to deliver the outer sheath to the internal body space, then a larger diameter, such as up to 40 French, and a shorter length, such as about 20 cm, may be appropriate. If a femoral approach is used, the outer sheath should have a smaller diameter and a greater length than for transapical access. Those of ordinary skill in the art can readily appreciate ranges of appropriate diameters and lengths for the outer sheath based on their understanding of patient physiology. All appropriate lengths and diameters are contemplated herein.

The inner sheath comprises an elongated tube portion that terminates in a distal retrieval end. The elongated tube portion is appropriately sized for being inserted into the subject's internal body space via the lumen of the outer sheath, i.e., it has an outer diameter that can fit within the lumen of the outer sheath. The length of the elongated tube portion can vary based on the length of the outer sheath, but must be sufficiently long so that the distal retrieval end can be advanced beyond the distal end of the outer sheath while the latter is positioned at the desired location within the subject's internal body space (where retrieval of the object is to occur), at the same time that the proximal end is available for operator control outside of the subject. Thus, when the outer sheath includes a handle, the inner sheath must be available for operator control and thereby extend towards the operator beyond the proximal end of the handle. Exemplary working lengths for the inner sheath are about 34 to about 42 inches, for example, about 34, about 35, about 36, about 37, about 38, about 39, about 40, about 41, or about 42 inches.

Figure 2:
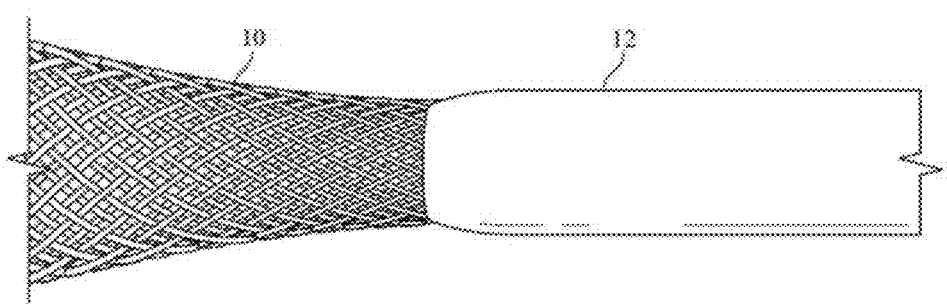
FIG. 2 is an image of one embodiment of the retrieval end comprising a wire weave that is bonded to the elongated tube portion of the inner sheath.

The retrieval end of the inner sheath is attached to or is part of the elongated tube portion. For example, the retrieval end may be bonded, annealed, or otherwise fixedly attached to the distal end of the elongated tube portion. FIG. 2 is an image of one embodiment of the retrieval end 10 comprising a wire weave that is bonded to the elongated tube portion 12 of the inner sheath. Although not illustrated in FIG. 2, the proximal portion of the retrieval end may overlap the elongated tube portion and the two components may be bonded to each other over the entire segment of overlap. For example, the retrieval end may overlap the elongated tube portion by about 0.5 cm, about 0.75 cm, about 1 cm, about 1.5 cm, about 2 cm, about 2.5 cm, or about 3 cm.

The elongated tube portion may be formed from any appropriate biocompatible material that, where necessary, can be bonded to the retrieval end. Exemplary materials include nitinol, stainless steel, cobalt chromium.

The retrieval end can be formed from any appropriate biocompatible material that can be compressed within the lumen of the outer sheath and can adopt the expanded state, preferably without any mechanical assistance, when the retrieval end is deployed into the subject's internal body space by exiting a distal end of the outer sheath. Shape memory alloys, such as nitinol, are suitable for these purposes, but any other material meeting the above-described requirements can be used.

Figure 6:
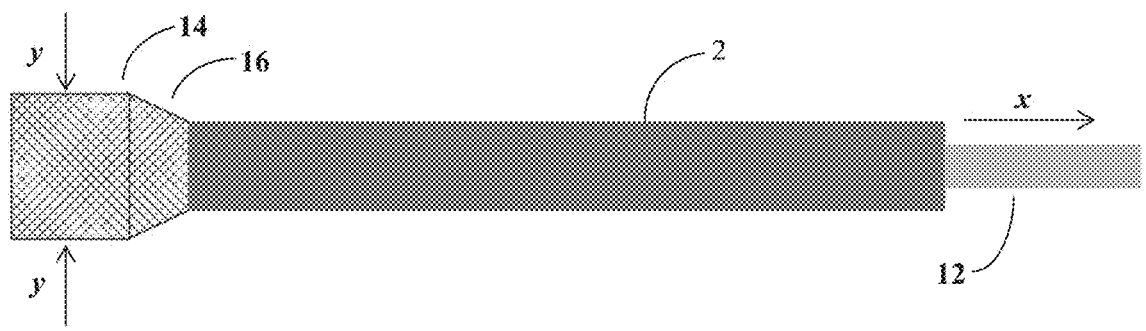
FIG. 6 illustrates the forces that are imposed at the retrieval end by withdrawing the inner sheath through the lumen of the outer sheath.
Figure 7A:
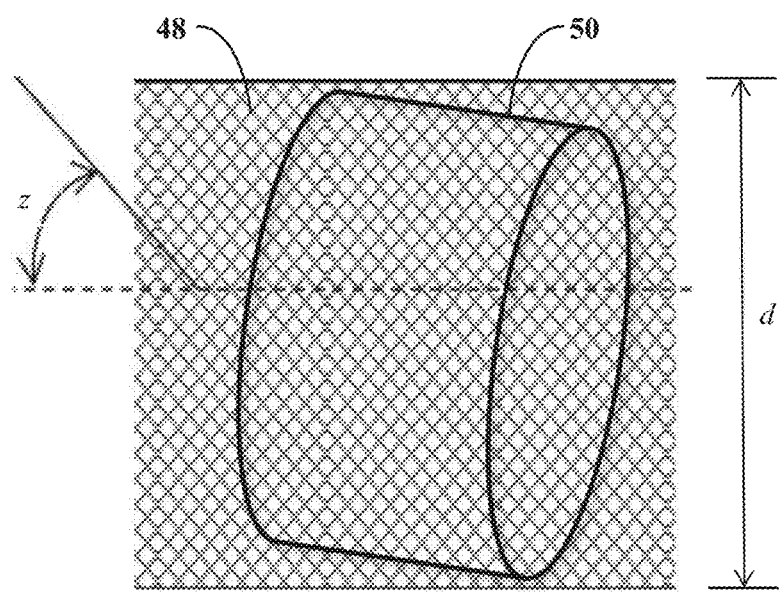
FIGS. 7A and 7B show how a retrieval end comprising a wire mesh changes shape and configuration during operation of the present systems and devices.
Figure 7B:
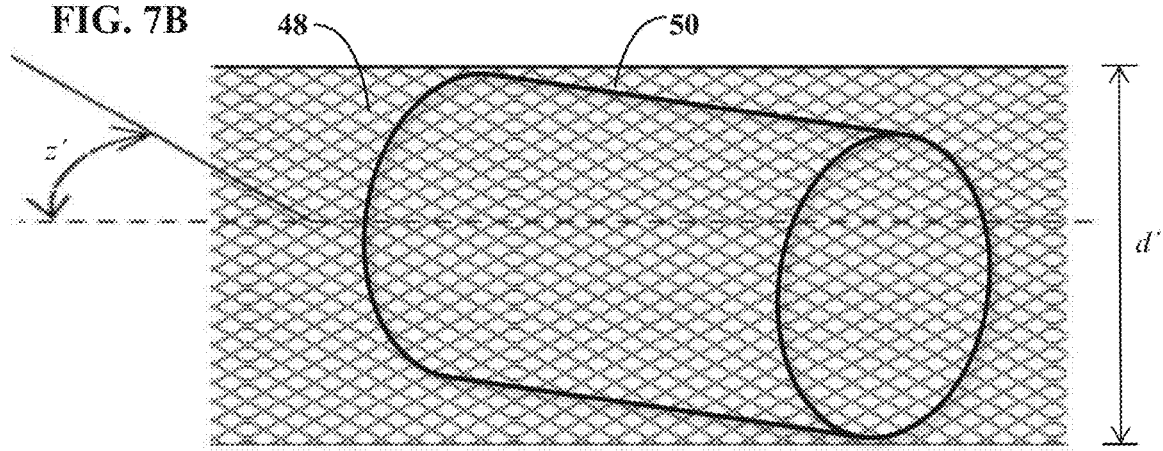

In addition, the inventors have surprisingly discovered that the retrieval end is such that when at least a portion of the retrieval end is withdrawn into the outer sheath following capture of the object, such as an endovascular device, within the interior space of the retrieval end, the retrieval end exerts an inward force that at least partially collapses or compresses the object. It is important to note that, as the retrieval end is withdrawn into the lumen of the outer sheath, the walls of the retrieval end, and not the walls of the outer sheath, exert a force that at least partially collapses or compresses the object. Thus, it is not necessary for any portion of the object to have entered the lumen of the outer sheath for there to be inward radial force that is directed against the object. Rather, as withdrawal of the retrieval end into the lumen of the outer sheath commences, the retrieval end begins to contract and to impose an inward radial force on any object within the interior space of the retrieval end, and, in the case of a collapsible object (such as an endovascular device, like a stent), this force can cause the object to collapse or compress even before any part of it enters the lumen of the outer sheath. Thus, the longitudinal force that is imposed on the inner sheath by the operator during the act of withdrawing the inner sheath through the lumen of the outer sheath translates into a radial compressive force by the retrieval end. This mechanism is described more fully below in connection with FIGS. 6 and 7.

In some embodiments, the retrieval end is formed from a wire weave, as shown in FIG. 2. When the retrieval end comprises a wire weave, one or more of the braiding angle, braid density, wire gauge, and other relevant characteristics are selected to fulfill each of the above-described requirements for the retrieval end. For example, the diameter of the wire that is used to form the wire weave may be from about 100 microns to about 300 microns, about 125 microns to about 300 microns, about 150 microns to about 300 microns, about 175 microns to about 275 microns, about 200 microns to about 275 microns, about 200 microns to about 250 microns, or about 200 microns to about 300 microns. Exemplary wire diameters include about 100 microns, about 120 microns, about 140 microns, about 160 microns, about 180 microns, about 200 microns, about 220 microns, about 230 microns, about 240 microns, about 250 microns, about 260 microns, about 270 microns, about 280 microns, about 290 microns, or about 300 microns. The wire diameter should be sufficient to withstand the forces that result from capturing and pressing against the object to be removed without breaking or significantly deforming. The wire diameter is also preferably small enough so that conventional braiding or weaving machines can be used to construct the wire weave. Braiding angles between radial and longitudinal may be used to form the wire weave, such that when the retrieval end is in the expanded state, it has the selected braiding angle. For example, the braiding angle of the wire weave when the retrieval end is in the expanded state may be about 45 degrees to about 90 degrees. Exemplary braiding angles are about 45 degrees to about 85 degrees, about 55 degrees to about 85 degrees, about 65 degrees to about 85 degrees, about 75 degrees to about 85 degrees, or about 45 degrees, about 55 degrees, about 60 degrees, about 65 degrees, about 70 degrees, about 75 degrees, about 80 degrees, about 85 degrees, or about 90 degrees. The braiding angle can decrease to about 5 degrees, about 10 degrees, about 15 degrees, about 20 degrees, about 25 degrees or about 30 degrees when the retrieval end is in a compressed state. The braiding angle and mechanism of operation of the retrieval end when formed from a wire weave is described more fully below in connection with FIGS. 7A and 7B. Preferably, the wire weave of the retrieval end adopts a closed end design, meaning that the wires at the edges of the weave (such as the lip of the retrieval end that forms the mouth) double back and thereby form loops, rather than protruding points of wire.

Figure 3:
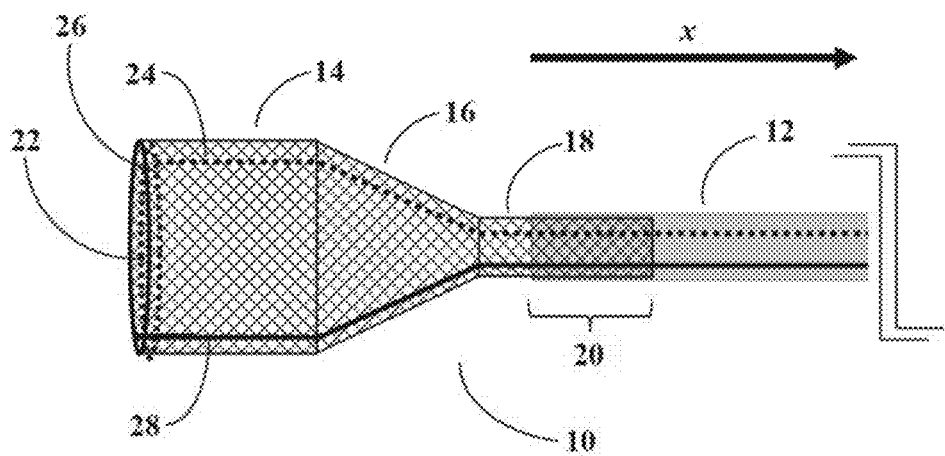
FIG. 3 depicts an embodiment of the retrieval end comprising a wire weave and including a control line and a suture line.

The overall shape and dimensions of the retrieval end are such that an object (of any desired type) can be drawn within the interior space of the retrieval end to the extent necessary that is required for accomplishing removal of the object from the subject's internal body space. Differently sized and shaped retrieval ends may be provided based on the nature of the object to be retrieved, and the nature of the internal body space to be accessed. Alternatively, a retrieval end may be sized and shaped so that it is capable of accommodating substantially any object that would require removal from a subject's internal body space. As shown in FIG. 3, in one embodiment, the retrieval end 10, shown in the expanded state, may include a main body portion 14, a tapering portion 16, and an attachment portion 18. The main body portion 14 is sized to accommodate an object within the interior space that is formed thereby. For example, the outer diameter of the main body portion 14 may be about 25 to about 35 mm. The tapering portion 16 links the main body portion to the attachment portion 18, which is so termed because it is attached to the elongated tube portion 12 of the inner sheath. As described above and as shown in FIG. 3, at least part of the attachment portion 18 of the retrieval end 10 may overlap the elongated tube portion 12, and the two components may be bonded to each other over the entire segment of overlap 20.

The main body portion 14 of retrieval end 10 terminates distally in a mouth 22, through which the object can be passed into the interior space of retrieval end 10 that the main body portion 14 defines. In FIG. 3, mouth 22 is shown in the open state. As described above, mouth 22 also possess a closed state (not shown) so that the object can be enclosed within the interior space defined by the main body portion 14 after passing through the mouth 22. In one embodiment, the mouth 22 can be transitioned from the open state to a closed state by a suture line 24 having a loop portion 26 that is positioned around the circumference of mouth 22. The suture line 24 is so termed because it draws closer together the distal edges of the retrieval end 10, i.e., that forms the mouth 22. The suture line may comprise any material and have any dimensions (e.g., diameter) that is suitable for this purpose. Suture line 24, when pulled in a distal to proximal direction (indicated by arrow x), causes contraction of the loop portion 26, which causes a corresponding contraction of mouth 22. When mouth 22 has been contracted to a sufficient extent, an object that was guided through mouth 22 into the interior space of the retrieval end 10 will be at least partially trapped within the interior space. Furthermore, the transitioning of the mouth 22 from the opened state to the closed state prevents the object from "watermelon seeding"

or otherwise escaping back out through the mouth 22 when withdrawal of the retrieval end 10 back into the outer sheath commences. It is noteworthy that the suture line 24 can transition the mouth 22 from the opened state to the closed state independently of whether the retrieval sheath and retrieval end has been at least partially withdrawn into the outer sheath. Although the suture line and loop portion represent a simple and reliable mechanism for transitioning the mouth to the closed state, any other mechanism that may be used for accomplishing the closed state of the mouth may be employed and is contemplated herein.

One example of an alternative mechanism for inducing the closed state of the mouth is to use a secondary catheter equipped with distal snare. When the object to be retrieved is in a vascular space, the catheter can be deployed using a second vascular access point. A further alternative involves the use of a manipulation tool or a snare that is deployed from the central lumen of the inner sheath.

The retrieval end 10 may also include a control line 28 that is attached at least to the part of main body portion 14 of the retrieval end 10 at the edge of the mouth, but may also or alternatively be attached to one or more other locations on the main body portion 14, and may also or alternatively be attached to one or more locations on the tapering portion 16, one or more locations on the attachment portion 18, or both. The control line 28 may be a wire or any other material that is suitable for providing longitudinal support for the retrieval end 10 while the object is being drawn into the retrieval end 10 via mouth 22, for changing the position of the mouth 22 of the retrieval end 10 within the subject's internal body space, or both. It is desirable for the control line 28 to provide longitudinal support for the retrieval end 10 because the process of drawing the object in to the interior space of the retrieval end 10 could otherwise render the retrieval end 10 vulnerable to unwanted crumpling or bunching up in the longitudinal direction. Use of the control line 28 to change the position of the mouth 22 within the subject's internal body space can provide the operator with the ability to guide the mouth 22 so that it is closer to or even positioned at least partially over the object to be removed. The control line 28 can more readily be used to position the mouth 22 at least partially over the object when the object has been gripped, grasped, grappled, or otherwise rendered stationary, or has been or moved to a desired position, each of which can be accomplished using one or more manipulation tools, which are described more fully below.

Figure 4A:
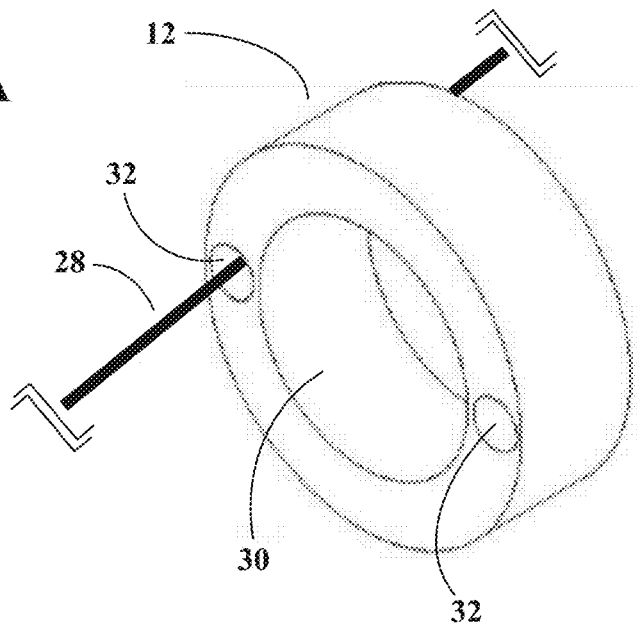
FIG. 4A is a cross-section of an exemplary inner sheath that includes a central main lumen and two dedicated side lumens.

The suture line 24, the control line 28, or both may be housed within dedicated lumens within the inner sheath 12. FIG. 4A is a cross-section of an exemplary inner sheath 12 that includes a central main lumen 30 and two dedicated side lumens 32. A control line 28 is shown as extending through one of the side lumens 32.

The present systems may include more than one control line. For example, the present systems may include two separate control lines, each being housed in the inner sheath and attached to the retrieval end as described above. Each control line may be housed in its own dedicated lumen in the inner sheath, or one, some, or all of the control lines and suture line may be housed within a central, main lumen of the inner sheath. In a further embodiment, one, some, or all of the control lines and suture line may be housed externally to the inner sheath.

Figure 4B:
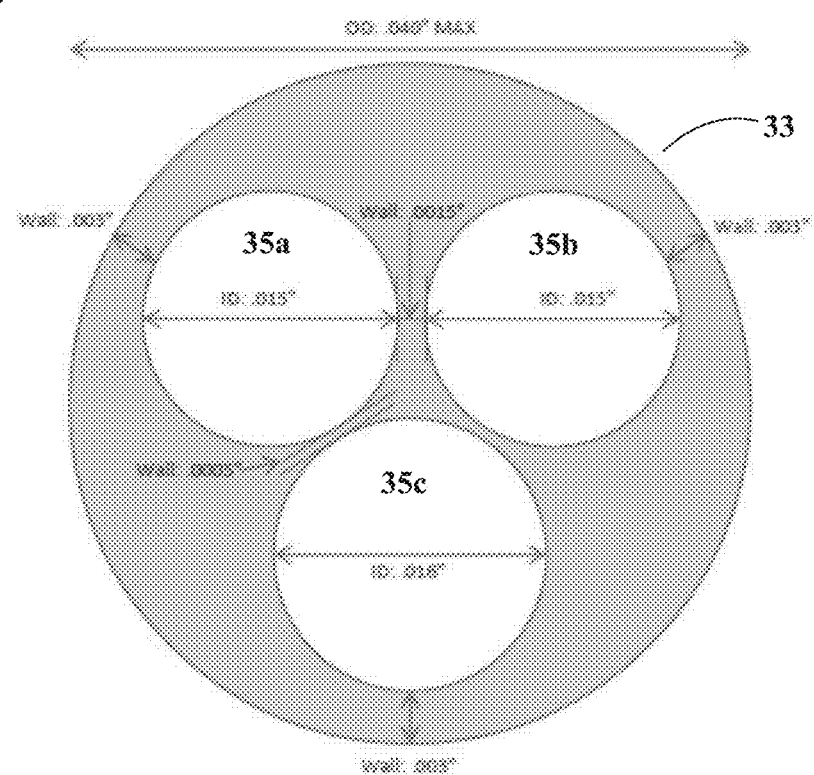
FIG. 4B is a cross section of a suture tube that can be deployed through a lumen of the inner sheath.
Figure 4C:
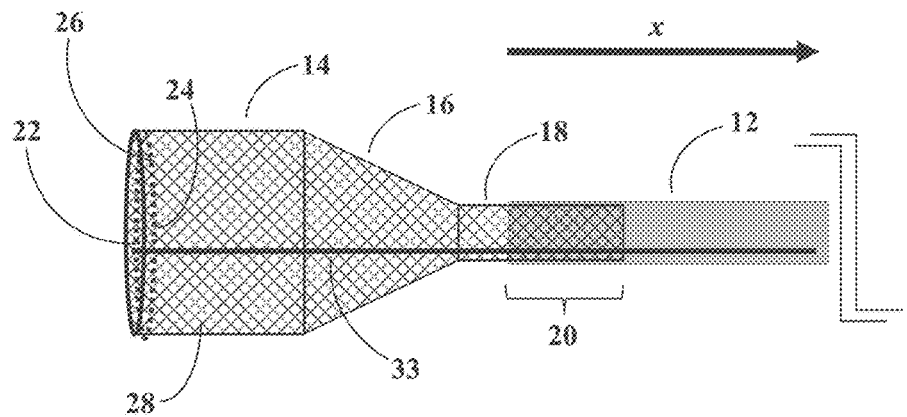
FIG. 4C shows how the suture tube is deployed relative to the retrieval end.

FIG. 4B depicts a cross section of a triple-lumen suture tube 33 that may be part of an alternative embodiment of the present systems. The measurements that are shown in FIG. 4B are illustrative only and are not intended to be limiting. A wire (not shown) may exit one of the lumens 35a at the distal end of the suture tube 33, and pass back into the suture tube 33 via a second of the lumens 35b at the distal end of the suture tube 33, thereby forming a looped attachment wire (not shown). The looped attachment wire is secured to the walls of the retrieval end in order to immobilize the suture tube 33 relative to the retrieval end. A suture line (not shown) is housed within the third lumen 35c, and exits that lumen at the distal end of suture tube. The suture line in such embodiments may have the same features and function in substantially the same manner as described above for suture line 24 in connection with FIG. 3. During operation of the system and as shown in FIG. 4C, the distal end of the suture tube 33 (the end from which the looped attachment wire and suture line 24 exit) is positioned as close to the mouth 22 of the retrieval end as possible, so that tightening of the suture line 24 will cause the mouth 22 to contract, but will not cause the mouth 24 to be pulled backwards towards the tapering portion 16 of the retrieval end to any substantial degree. The suture tube 33 may be housed within the main lumen or a dedicated lumen of the inner sheath. If the inner sheath possesses only a single lumen, then the suture tube 33 is housed within and exits from the distal end of that lumen.

As described above, FIG. 3 depicts an exemplary retrieval end in the expanded state. The retrieval end according to the present systems can also adopt one or more compressed states. For example, the retrieval end adopts a compressed state when it is housed within the lumen of the outer sheath during delivery to the subject's internal body space and before deployment therein. The retrieval end adopts a second compressed state when it is withdrawn back into the lumen of the outer sheath following capture of the object within the interior space of the retrieval end. Understandably, because of the presence of the object within the retrieval end, the second compressed state will be somewhat different than the compressed state that the retrieval end adopts when it is housed within the lumen of the outers sheath before it is initially deployed within the subject's internal body space. However, compressed state that the retrieval end adopts will permit the retrieval end to fit within the lumen of the outer sheath.

Figure 5A:
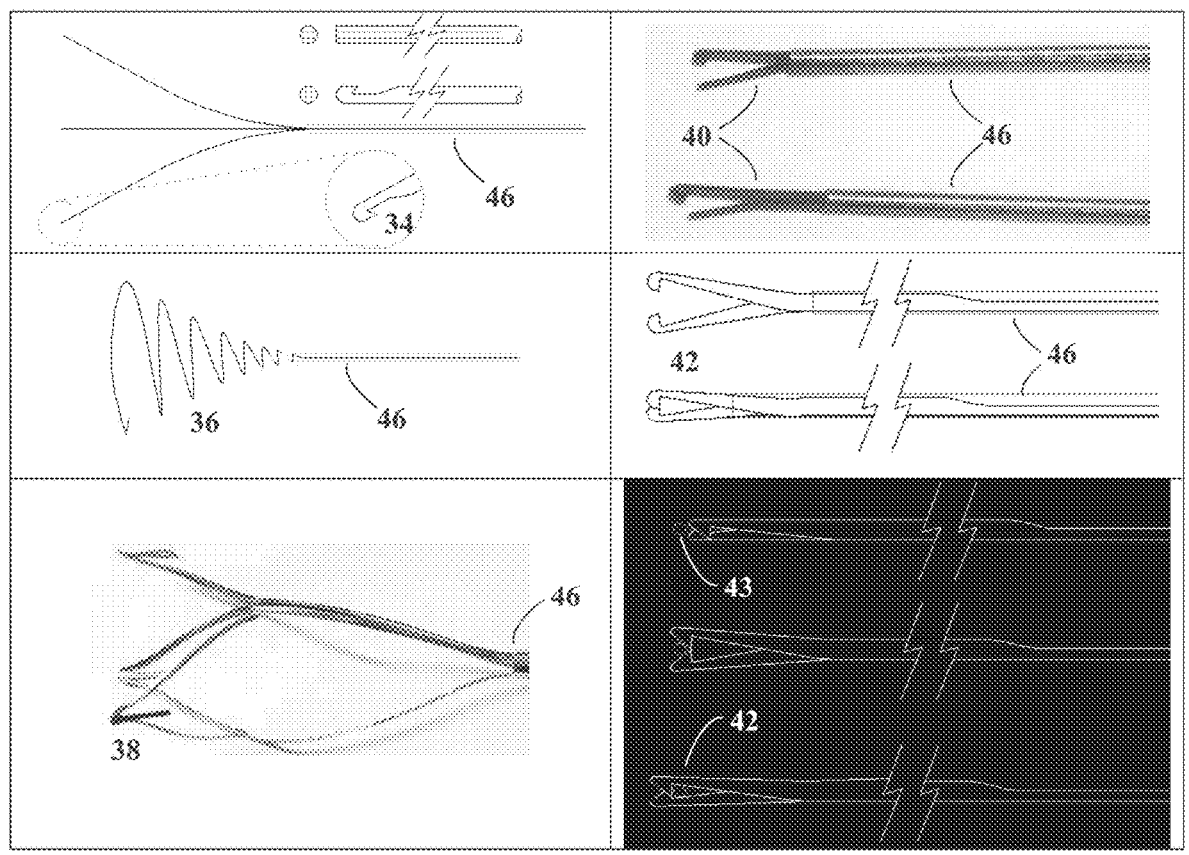
FIGS. 5A and 5B depict various embodiments of manipulation tools for use in the presently disclosed systems.
Figure 5B:
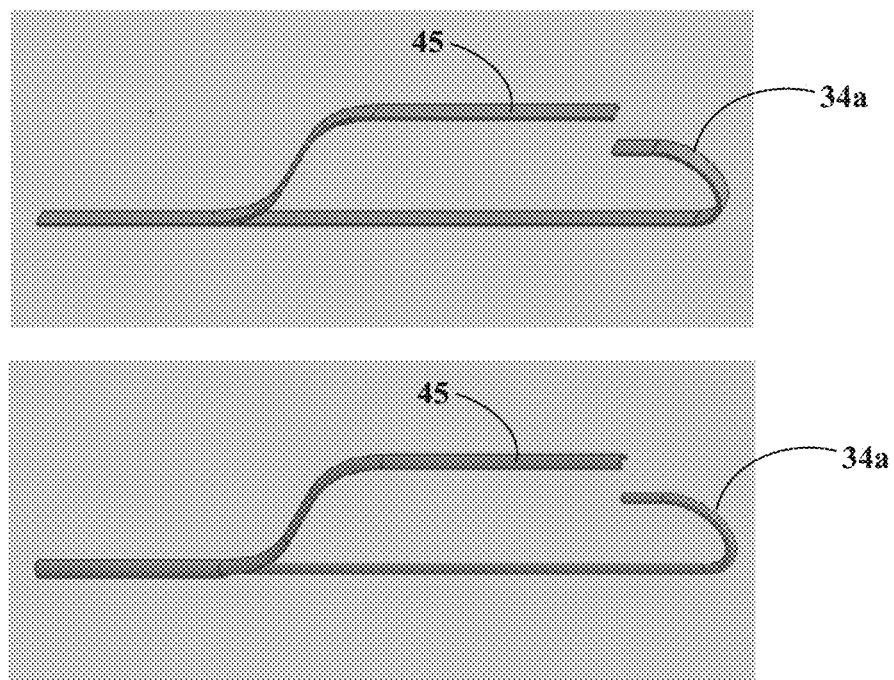

The present systems may further comprise one or more manipulation tools for gripping, grasping, grappling, ensnaring, moving, or otherwise capturing, changing the orientation, or manipulating the object. The manipulation tools are preferably deployable into the subject's internal body space via a lumen in the inner sheath. For example, the manipulation tools may be deployable via a central main lumen 30, as in FIGS. 4A and 4B. The manipulation tools may include hooks, snares, grippers, loops, grapples, scissors, clips, or any other, that are mounted on the end of a cable or other elongated structure having length that is capable of reaching the relevant body space within the subject while being controllable by the operator. FIG. 5A depicts various embodiments of manipulation tools, including hooks 34, spiral loops 36, grapples 38, grippers 40, "scissors" (non-cutting) that are biased open 42, and "scissors" that are biased closed 44. Further examples of manipulation tools, both featuring a hook 34a and a pin 45, are shown in FIG. 5B.

To the extent that the manipulation tools include moving parts, such as in the case of a scissor- or clip-like embodiment, manipulation tools may be actuated by a cable or any other mechanism that is controlled by the operator. The cable or other elongated material onto which the manipulation tool may be mounted can be housed within tubing into which the manipulation tool can be withdrawn and from which the manipulation tool can be deployed as desired.

FIG. 5A shows the tubing portion 46 as associated with various embodiments of the manipulation tools. The tubing portion 46 may play a role in deploying or actuating a manipulation tool. For example, the manipulation tool bearing hooks 34 may include a single wire that is split into three filaments, each filament terminating in a hook 34. The manipulation tool is housed within tubing 46 before deployment, and deployment results in separation of the filaments (shown). In one embodiment, the hooks 34 are oriented towards a single central axis when the manipulation tool is housed within tubing 46, and turn radially outwards when the manipulation tool is deployed. For the manipulation tool bearing grippers 40 or scissors 42 that are biased open, deployment of the manipulation tool from the tubing 46 causes the grippers 40 or scissors 42 to open.

For the manipulation tool bearing scissors 44 that are biased closed, advancing the scissors 44 over an object 43 such as a wire section of a stent causes the scissors to open (see middle image) and then close again after the object 43 is grasped between the elements of the scissors 44 (see bottom image).

The present systems may also comprise a loading tube for facilitating insertion of the inner sheath within the outer sheath. For example, the loading tube may be a cylindrical tube having a lumen, a distal end, and a proximal end into which the inner sheath can be inserted so that the retrieval end adopts a compressed state. The proximal end of the loading tube may include a flared or funnel-shaped portion permits easier insertion of the retrieval end. As the retrieval end is pushed further into the loading tube, the retrieval end adopts a compressed state. The distal end of the loading tube may be positioned so that it is coterminous with a proximal end of the outer sheath, or with the hemostasis valve that in which a proximal end of the outer sheath is housed (described more fully above). The retrieval end of the inner sheath may be advanced beyond the distal end of the loading tube until it enters the lumen of the outer sheath, and then the inner sheath may be advanced still further so that the tube portion of the inner sheath enters the outer sheath.

The present systems may further include a dilator for facilitating delivery of the outer sheath into the subject's internal body space. For example, the process for delivering the outer sheath may begin with directing a guidewire to the site of interest within the subject's body. The guidewire may be directed via fluoroscopy. A dilator, preferably constructed from a material that is supple enough to avoid damaging the subject's physiology and to permit flexible guidance to the site of interest, is advanced over the guidewire until its distal tip, which may feature a taper in order to enhance the ease of guidance through the subject's body (e.g., vasculature or gastrointestinal tract), reaches the site of interest. The outer diameter of the dilator is such that the outer sheath can fit over it, and indeed, the outer sheath can be guided over the dilator until the distal tip of the outer sheath reaches the site of interest.

The present disclosure also relates to methods for percutaneously retrieving an object, such as an endovascular device, within a subject's internal body space, the methods comprising: delivering to the subject's internal body space outer sheath having a lumen; introducing an inner sheath into the lumen of the outer sheath, the inner sheath comprising a distal retrieval end having one or more compressed states and an expanded state, the retrieval end adopting one of the compressed states when the retrieval end is housed within the lumen of the outer sheath, and adopting the expanded state when the retrieval end is deployed into the subject's internal body space by exiting a distal end of the outer sheath, the retrieval end having a mouth through which the object can be passed into an interior space within the retrieval end when the retrieval end is in the expanded state, the mouth being adjustable between an opened state and a closed state so that the object can be enclosed within the interior space after passing through the mouth of the retrieval end; advancing the inner sheath through the lumen of the outer sheath until the retrieval end is deployed into the subject's vasculature by exiting the distal end of the outer sheath; capturing the object at least partially within the interior space of the retrieval end; at least partially closing the mouth of the retrieval end in order to enclose the object within the interior space of the retrieval end; withdrawing the inner sheath through the lumen of the outer sheath until the retrieval end exerts an inward force that at least partially collapses or compresses the object; and, withdrawing the retrieval end into the lumen of the outer sheath, thereby removing the object from the subject's internal body space.

Each of the characteristics of the outer sheath, inner sheath (including the retrieval end), and associated elements and components (such as the loader tube, dilator tube, manipulation tools, suture line, and control line) that are described above in connection with the presently disclosed systems are fully applicable to the corresponding components in the present methods.

The inner sheath may be introduced into the lumen of the outer sheath by introducing the inner sheath into the lumen of a loader tube via a proximal end of the loader tube; advancing inner sheath through the lumen of the loader tube to a distal end thereof until the inner sheath exits the distal end of the loader tube and enters the lumen of the outer sheath via a proximal end of the outer sheath; and, advancing the inner sheath until the retrieval end of the inner sheath approaches, but does not exit, the distal end of the outer sheath.

Following deployment of the retrieval end into the subject's internal body space, the position of the retrieval end may be adjusted relative to the object by use of a control line that is affixed to the retrieval end. For example, the control line may be used to position the retrieval end so that the object is proximate to the mouth of the retrieval end. The control line may also be used to position the mouth over at least a portion of the object. These and other uses of the control line are described above in connection with the presently disclosed systems. One configuration for attaching the control line to the retrieval end is to loop the line around several wires at the mouth of the retrieval end, and weld the control line back on itself at the point where the loop around the mouth is complete. This approach advantageously preserves the ability of the braided wires of the retrieval to move independently. On the other hand, welding or gluing the control line to groups of wires of the retrieval end was found to immobilize the wires, thereby affecting the ability of the retrieval end to fully reduce in diameter during withdrawal of the retrieval end into the inner sheath. Thus, the preferred approaches for securing the control line to the retrieval end do not inhibit the ability of the retrieval end to operate as described herein.

The present methods may further comprise, following deployment of the retrieval end into the subject's internal body space, advancing through a lumen of the inner sheath a manipulation tool that grips, grasps, grapples, ensnares, moves, captures, changes the orientation, or manipulates the object in order to assist in the step of capturing the object at least partially within the interior space of the retrieval end. When the methods include this step, they may also include the step of adjusting the position of the retrieval end relative to the object by use of a control line that is affixed to the retrieval end, in order to place the mouth of the retrieval end proximate to the object at the same time that the manipulation tool grips, grasps, grapples, ensnares, moves, captures, changes the orientation, or manipulates the object.

As described above, when the presently disclosed systems and methods are used to capture the object within the interior space of the retrieval end, the inner sheath may be withdrawn through the lumen of the outer sheath until the retrieval end exerts an inward force that at least partially collapses or compresses the object. Thus, the longitudinal force that is imposed on the inner sheath by the operator during the act of withdrawing the inner sheath through the lumen of the outer sheath translates into a radial compressive force by the retrieval end. This effect is shown in FIGS. 6A and 6B, wherein arrow x indicates the withdrawal force that is imposed by the operator by the act of withdrawing the withdrawing the inner sheath 12 through the lumen of the outer sheath 2, and the arrows labeled y indicates the resulting inward compressive force at the retrieval end 14. In the figure, the retrieval end 14 has been partially withdrawn (up and including part of the tapering portion) into the lumen of the outer sheath. Withdrawal of the inner sheath into the outer sheath until the retrieval end is at least partially drawn into outer sheath can cause the retrieval end to elongate and the diameter of the retrieval end to decrease. The present inventors have surprisingly discovered that the resulting inwardly directed forces that are imposed on the object are sufficient to at least partially collapse or compress the object. In fact, the forces that are imposed on the object are sufficient to collapse or compress the object to the extent required to be completely drawn within the lumen of the outer sheath along with the retrieval end, so that the object can be completely removed from the subject via the outer sheath. As noted previously, as the retrieval end is withdrawn into the lumen of the outer sheath, the walls of the retrieval end, and not the walls of the outer sheath, exert a force that at least partially collapses or compresses the object. Thus, it is not necessary for any portion of the object to have entered the lumen of the outer sheath for there to be inward radial force that is directed against the object.

When the retrieval end comprises a wire mesh, withdrawal of the inner sheath into the outer sheath until the retrieval end is at least partially drawn into outer sheath can cause the braiding angle of the wire mesh to decrease pursuant to the elongation and decrease of the diameter of the retrieval end. This effect is shown in FIGS. 6A and 6B, in which 6A shows a section of wire mesh 48 representing a portion of an exemplary retrieval end when the retrieval end is in the expanded state prior to withdrawal of any portion thereof into the outer sheath. The wire mesh 48 under these conditions has a braiding angle of z and a diameter of d. Object 50, such as an endovascular device, is held within the illustrated portion of the retrieval end. When the inner sheath (not shown) and at least a portion of the retrieval end is withdrawn into the outer sheath (not shown), the retrieval end begins to transition to a compressed state, experiences elongation, and, as shown in FIG. 6B, the braiding angle decreases from z to z', the diameter decreases from d to d', and object 50 is at least partially collapsed due to the forces that are imposed on it by the walls of the retrieval end.

Thus, in accordance with the presently disclosed systems, methods, and devices, the retrieval end may comprise a wire weave having a first braiding angle when the retrieval end is in the expanded state and before withdrawal of any portion of the retrieval end into the outer sheath. In addition, the retrieval end may be such that it elongates and the braiding angle of the wire weave decreases from the first braiding angle to a second braiding angle in response to withdrawal of at least a portion of the retrieval end of the inner sheath into the outer sheath.

The present disclosure also pertains to devices for percutaneously retrieving an object from a subject's internal body space, the devices comprising an elongated tube portion that terminates in a distal retrieval end, the distal retrieval end comprising a wire weave and having one or more compressed states and an expanded state, the retrieval end adopting one of the compressed states when the retrieval end is housed within the lumen of an outer sheath, and adopting the expanded state when the retrieval end is deployed into the subject's internal body space by exiting a distal end of the outer sheath, the retrieval end having a mouth through which the object can be passed into an interior space within the retrieval end when the retrieval end is in the expanded state, the mouth being adjustable between an opened state and a closed state so that the object can be enclosed within the interior space after passing through the mouth of the retrieval end.

The elongated tube portion and retrieval end of the present devices may have any of the characteristics as described above in connection with the corresponding components of the present systems.

The closed state of the mouth refers to any degree of contraction of the mouth that is sufficient to prevent the object from "watermelon seeding" or otherwise escaping back out through the mouth during the process of removing the object from the subject. The mouth of the retrieval end may adopt the closed state at the will of the operator. In other words, the present devices may include components that permit the mouth to transition into the substantially closed state independently of whether the retrieval end is being transitioned out of the expanded state, and independently of whether the retrieval end is being withdrawn out of the relevant body space, e.g., is being withdrawn into an outer sheath that houses the elongated tube of the present devices. An exemplary component for accomplishing this end is a suture line of the type described above in connection with the present systems.

Accordingly, the instant devices may further comprise a suture line having a loop portion that is positioned around the circumference of the mouth of the retrieval end and that is used to transition the mouth between the opened state and the closed state. The suture line may be housed within a lumen in the elongated tube portion. The devices may also or alternatively include a control line that is affixed to the retrieval end for changing the position of the mouth of the retrieval end within the subject's internal body space, for providing longitudinal support for the retrieval end while the object is being drawn into the retrieval end, or both. The control line may be housed within a lumen in the inner sheath. In order to accommodate a control wire, a suture line, manipulation tools, or other implements or components, the elongated tube portion may include one, two, three, or four interior lumens. A cross-section of an embodiment of the elongated tube portion that includes three separate interior lumens is shown in FIGS. 4A and 4B.

The retrieval end of the present devices can exert an inward force that at least partially collapses or compresses the object. This occurs when the retrieval end is being transitioned out of the expanded state, such as when the elongated tube portion and the retrieval end are withdrawn through the outer sheath. The mechanism of collapsing or compressing the object by the retrieval end is described above in connection with the presently disclosed systems and methods.

The present disclosure also pertains to additional devices for percutaneously retrieving an object from a subject's internal body space, the devices comprising an elongated tube for introduction into the subject that terminates in a retrieval end, the retrieval end comprising a wire weave, the retrieval end being expandable into an expanded state, the retrieval end further having a mouth through which the object can be passed into a space within the retrieval end when the retrieval end is in the expanded state, the mouth being adjustable between an opened state and a substantially closed state so that the object can be retained within retrieval end after passing through the mouth of the retrieval end.

As used herein, "substantially closed" means that the mouth is closed to any extent necessary to prevent the object from "watermelon seeding" or otherwise escaping back out through the mouth during the process of removing the object from the subject. The mouth of the retrieval end may adopt the substantially closed state at the will of the operator. In other words, the present devices may include components that permit the mouth to transition into the substantially closed state independently of whether the retrieval end is being transitioned out of the expanded state (e.g., to an at least partially collapsed state), and independently of whether the retrieval end is being withdrawn out of the relevant body space, e.g., is being withdrawn into an outer sheath that houses the elongated tube of the present devices. An exemplary component for accomplishing this end is a suture line of the type described above in connection with the present systems.

The retrieval end of the instant devices may be collapsed into a collapsed state following retention of the object within the retrieval end. For example, this may be accomplished by withdrawing the retrieval end into an outer sheath that houses the elongated tube to which the retrieval end is attached. The collapsing of the retrieval end can collapse or compress the object that is retained within it. In particular, the retrieval end of the present devices can exert an inward force that at least partially collapses or compresses the object. This occurs when the retrieval end is being transitioned out of the expanded state, such as when the elongated tube portion and the retrieval end are withdrawn through an outer sheath that houses the elongated tube portion and retrieval end. The wire weave of the retrieval end has a first braiding angle when the retrieval end is in the expanded state. When the retrieval end is transitioned from the expanded state to an at least partially collapsed state, the retrieval end elongates and the braiding angle of the wire weave decreases from the first braiding angle to a second braiding angle.

Figure 8A:
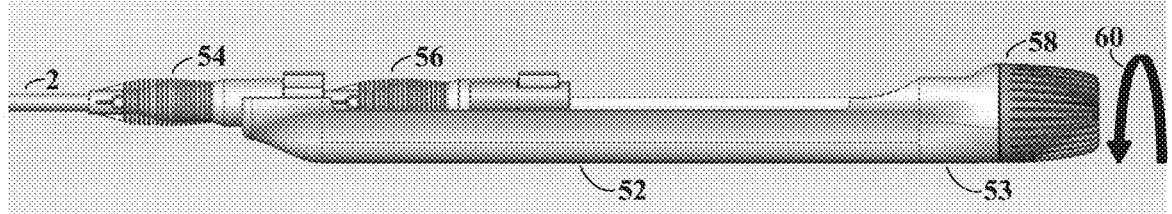
FIGS. 8A and 8B illustrate a mechanism for withdrawing the inner sheath and thereby the retrieval end from the subject's inner body space in a controlled, gradual manner.
Figure 8B:
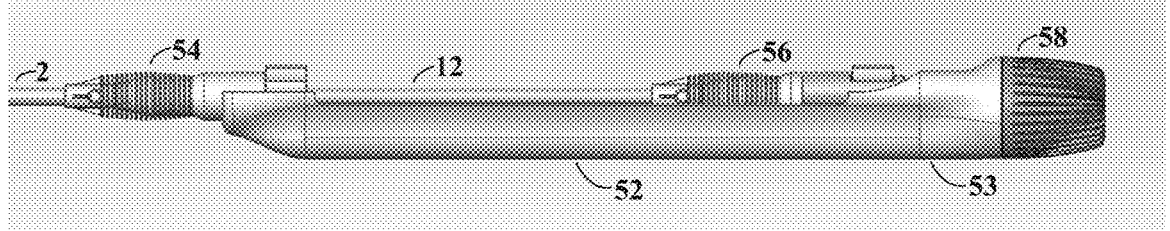

The systems according to the present disclosure may include a specialized mechanism for withdrawing the inner sheath in a controlled, gradual manner. Absent such a mechanism, the risk exists that the inner sheath could accidentally be jerked in the direction of the operator in a manner that could cause injury to the subject. FIGS. 8A and 8B depict an exemplary mechanism that includes a housing 52 that accommodates outer sheath handle 54 and inner sheath handle 56, that are attached to outer sheath 2 and inner sheath 12, respectively. Housing 52 may have an open design, as shown in FIGS. 8A and FIG. 8B, or may completely enclose handles 54, 56, as long as the housing can be opened in order to provide access to the handles. When handle 56 is at a forward location within housing 52, indicating that the inner sheath 12 and retrieval end (not shown) are at their respective maximal forward positions (i.e., the retrieval end is fully deployed in the subject's body space) (FIG. 8A), knob 58 can be rotated in the direction indicated by arrow 60 in order to begin controlled, gradual withdrawal of handle 56 attached to inner sheath 12 towards the rear end 53 of the housing 52. Continued rotation of knob 58 in the direction of arrow 60 will eventually result in withdrawal of handle 56 to its maximal withdrawn position, as shown in FIG. 8B. At this point, the retrieval end will have been completely withdrawn into the lumen of outer sheath 2.

Additional details regarding the mechanism of collapsing or compressing the object by the retrieval end is described above in connection with the presently disclosed systems and methods.

EXAMPLES

The following examples are set forth so as to provide those of ordinary skill in the art with a complete disclosure and description of how the methods, compositions, and components claimed herein are made and evaluated, and are intended to be purely exemplary of the invention and are not intended to limit the scope of what the inventors regard as their invention.

Example 1—Design of Retrieval End

Finite element analysis (FEA) has become established as a powerful method for mathematically modeling complex medical devices with the purpose of understanding force and stress when the device is in use a dynamic, in vivo environment. An embodiment of the retrieval end was designed to be inserted into a body space with the purpose of retrieval of objects, for example, that have been malpositioned or have embolized, via the use of a wire woven basket. The mechanism of retrieval uses a radial compressive force that is imposed by the braided wire structure as it is retracted into an outer sheath. As illustrated in FIGS. 6A and FIG. 6B, the retraction force ($F_R$) at the proximal end of the sheath is translated to the radial compressive force ($F_C$) of the braided structure at the distal end, and in an ideal model, $F_R=F_C$. However, there is a change in the ratio of $F_C$ to $F_R$ as system friction ($F_F$) and the force of the retraction of the basket structure itself ($F_B$) are included: $F_R=F_C+F_F+F_B$. Multiple variables can affect the dynamic of this force equation such as the number of wires, wire diameter, material properties and braid angle were introduced and modified. The present inventors constructed a braid configuration to minimize the retraction force while maximizing the radial compressive force.

Braid geometries are constructed, and retraction through a rigid tube (outer sheath) are simulated using a commercial FEA software (Abaqus). In addition, a proxy geometric shape is created to simulate a device being retrieved. Once the numerical model has been built, it is calibrated by performing actual bench testing of devices already built. Due to the unique temperature-dependent properties of Nitinol, it is desirable to perform this testing at body temperature: 37° C. The calibration is accomplished in a two-step approach. First, the retraction force of the braid into the outer sheath is measured by attaching a force gage to the proximal end of the retrieval sheath and pulling the braid into the outer sheath. From this, the force along with the distance of travel of the sheath is measured and a graph is plotted. This allows for all of the system forces, all those not related to the retrieval of an actual device, to be quantified (i.e. $F_F$ and $F_B$). Second, a Nitinol device is circumferentially reduced in diameter in radial expansion force testing equipment (Machine Solutions Inc. RX650) which has a temperature controlled chamber with PC control and data capture. The radial resistive force as the device is being compressed is measured, and the diameter of the device and a graph is generated. This allows for the isolation of the requirement for radial compression force at the retrieval end. The geometric shape is then generated in the FEA model replicating these force characteristics. With these calibrations in place, relative comparisons are demonstrated using different braid constructions by contrasting differences in the system and its radial compressive forces ($F_C$).

By modifying the variables with a calibrated numerical model, the interactions of the various components are modeled to minimize $F_F$ and $F_B$ and optimize the ratio of $F_C$ to $F_R$. Then, by utilizing the MSI RX650 and characterizing the radial resistive forces of commercially available transcatheter aortic valves replacement (TAVR) devices, the ability of the retrieval system to compress these devices is predicted. Finally, the best performing braid constructions as predicted by FEA are produced. These devices are built into simplified catheter constructions and tested in a manner consistent with the calibration testing as described above: a gauge is attached to the retrieval catheter and retracted into the outer sheath measuring force and travel distance. However, in these tests, a device is placed in the wire woven basket and as the basket/device combination are retracted into the outer sheath, the force to retrieve a device ($F_R$) is measured.

Example 2—Retrieval of Stent Containing Mitral Valve Prosthesis

A subject presents with a dislodged stent-based mitral valve prosthesis, and based on the availability of more advanced designs, the decision is made to remove the dislodged device and install a replacement. The subject is placed under general anesthesia, the femoral vein (right or left) is accessed, and a vascular sheath is inserted using the Seldinger technique. The atrial septum is crossed via standard transseptal technique, and an atrial hole is created/enlarged via balloon dilation septostomy (10-15 mm angioplasty balloon). Subsequently, guidewire is carefully shaped to and then positioned in the left ventricle through the newly created atrial hole. The femoral venous access site is made larger or "dilated up" with sequentially larger vascular dilators sized appropriately to match the diameter of the system for removing the device.

A dilator made from 25D PebaSlix™ with $BaSO_4$ extrusion is advanced over the wire, into the femoral vein, through the venous system, across the atrial septal defect and then positioned at the level of the mitral annulus using ECHO (transesophageal and or Intracardiac) and fluoroscopic guidance. The steering mechanism is then used to navigate the leading tip of the outer sheath, which bears a platinum marker band and has a 27 French inner diameter, 30 French outer diameter, and an overall length of 31.75 inches (including a handle portion), through the vasculature and across the septum. An inner sheath is housed within the lumen of the outer sheath. The inner sheath features three internal lumens, including a central main lumen and two side lumens for housing a suture line and a control line, has a working length of 38.5 inches (excluding the handle portion), and an outer diameter of 26 French. The inner sheath features an elongated tube portion and a retrieval end that is formed from a wire weave, the wire that forms the weave having a diameter of 230 μm, and the wire weave having a closed end design and featuring a 45° braiding angle when the retrieval end is in the expanded state. The mouth of the retrieval end has a 35 mm outer diameter when the retrieval end is in the expanded state. In other embodiments, the diameter of mouth 22 of the retrieval end is customized by application (e.g., 35 or 40 mm for use in the ventricle, 10-15 mm for use in the iliac). Those of ordinary skill in the art can readily select the dimensions of the retrieval end in accordance with the desired use and location of use. The retrieval end features a main body portion, a tapering portion, and an attachment portion that is bonded to the distal end of the elongated tube portion of the inner sheath. The main body portion of the retrieval end has longitudinal width of 50 mm, the tapering portion has a longitudinal width of 50 mm, and the attachment portion has a longitudinal width of 30 mm, of which a 20 mm wide section overlaps and is bonded to the elongated tube portion.

When the distal tip of the outer sheath reaches the mitral annulus, the inner sheath is advanced through the lumen of the outer sheath until the retrieval end is deployed into the portion of the left atrium adjacent the mitral valve annulus. A manipulation tool featuring a tri-filament design, each filament being formed from nitinol and terminating in a hook, is advanced through the central lumen of the inner sheath until it is deployed into the left atrium. Under fluoroscopic guidance, the manipulation tool is steered until at least one of the hooks engages the stent portion of the mitral valve prosthesis, and then withdrawn into the retrieval end and inner sheath lumen to the extent necessary to position the prosthesis within the internal space of the retrieval end. During this process, a control line is used to change the orientation of the mouth of the retrieval end so that it is positioned directly opposite the mitral valve prosthesis.

Once the prosthesis is positioned within the internal space of the retrieval end, the manipulation tools are disengaged from the prosthesis and withdrawn back through the lumen of the inner sheath, and the operator pulls the suture line so that a loop portion thereof, which is attached to the retrieval end along circumference of the mouth, transitions the mouth from the open state to the closed state. Then, the inner sheath is withdrawn through the lumen of the outer sheath until the retrieval end partially enters that lumen. At this point, the retrieval end begins to elongate and the braiding angle of the wire weave decreases from the braiding angle of the retrieval end in the expanded state to a second, smaller braiding angle. As more of the retrieval end (but not the valve prosthesis) is withdrawn through the lumen of the outer sheath, the portions of retrieval end remaining outside of the outer sheath continued to elongate, and the braiding angle of such portions continues to decrease. At the same time, the wire weave spirals around the prosthesis, and the diameter of the retrieval end continues to decrease and impose an inward force on the prosthesis until the prosthesis at least partially collapses. When the degree of collapse is such that the diameter of the device as oriented within the interior space of the retrieval end is less than the inner diameter of the outer sheath's lumen, the device and the portions of the retrieval end that surround it are suddenly drawn into the lumen of the outer sheath. When this occurs, the inner sheath, with the retrieval end and at least partially collapsed device can be withdrawn through the entire length of the lumen of the outer sheath, and outside of the subject.

Example 3—Additional Retrieval Ends

Figure 9A:
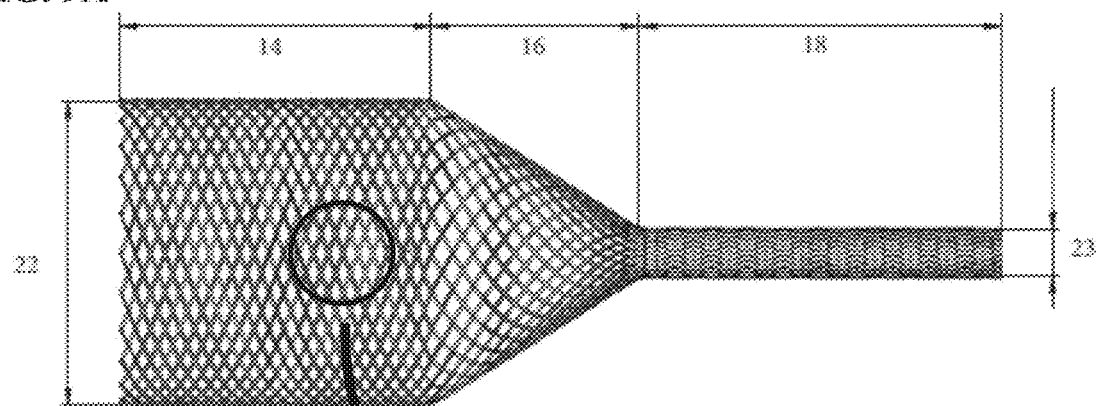
FIGS. 9A and 9B provide an illustration of further embodiments of retrieval ends and of a magnified portion of the retrieval end, respectively.
Figure 9B:
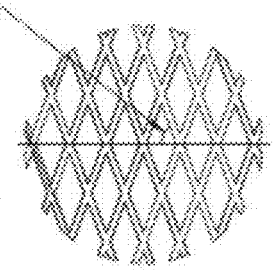

Three exemplary retrieval ends were formed from a wire weave, in which the braiding angle, braid density, wire gauge, and other relevant characteristics were selected to fulfill each of the above-described requirements for the retrieval end. The objective of forming three different retrieval ends was to be compatible with one of three different outer sheath sizes, 12 French, 18 French, or 24 French (inner diameter). FIG. 9A provides a generalized illustration of the retrieval ends that were produced, wherein each example included a mouth 22 having a desired diameter, a main body portion 14, a tapering portion 16, an attachment portion 18, and an attachment portion terminus 23 having a desired diameter. FIG. 9B illustrates a section of main body portion 14 that is magnified by approximately 5× in order to show additional detail of the wire weave, including how the braiding angle z was measured. In each of the examples, the main body portion 14 had a length of 30±3 mm, the tapering portion had a length of 20±3 mm, and the attachment portion 18 had a length of 35±3 mm. Table 1, below, describes other characteristics of each of the three retrieval ends.

TABLE 1

| Outer Sheath Size | Diameter Section 23 | Diameter Mouth 22 | Initial Wire Diameter | Picks Per Centimeter* Portion 14 | Braiding Angle, Portion 14 | Number of Wire Ends |
|---|---|---|---|---|---|---|
| 12F | 4.0 ± 0.5 mm | 29.0 ± 3.0 mm | 0.229 ± 0.008 mm | 11-21 | 80° ± 3° | 48 |
| 18F | 5.6 ± 0.5 mm | 29.0 ± 3.0 mm | 0.254 ± 0.008 mm | 11-21 | 80° ± 3° | 48 |
| 24F | 5.6 ± 0.5 mm | 29.0 ± 3.0 mm | 0.254 ± 0.008 mm | 11-21 | 80° ± 3° | 48 |

*A pick is a point where two wires of the wire mesh cross each other. 2.54 picks per cm = 1 pick per inch In further embodiment (not illustrated), the main body portion 14 had a length of 50 mm, the tapering portion 16 had a length of 50 mm, and the attachment portion 18 had a length of 30 mm. In the same embodiment, the diameter of the mouth 22 was 35 mm, and the diameter of the attachment portion terminus 23 was 10 mm. In further embodiments, the number of wire ends is 12, 24, or 96.

What is claimed:

1. A system for percutaneous retrieval of an endovascular device within a subject's internal body space comprising:
    an outer sheath having a lumen and being adapted for insertion into a subject's internal body space;
    an inner sheath that is adapted for insertion into the subject's internal body space via the lumen of the outer sheath, the inner sheath comprising
        a distal retrieval end comprising a wire weave formed from wires and having one or more compressed states and an expanded state, the retrieval end adopting one of the compressed states when the retrieval end is housed within the lumen of the outer sheath, and adopting the expanded state when the retrieval end is deployed into the subject's internal body space by exiting a distal end of the outer sheath,
        the retrieval end having a mouth through which the endovascular device can be passed into an interior space within the retrieval end when the retrieval end is in the expanded state, the mouth being adjustable between an opened state and a closed state so that the endovascular device can be enclosed within the interior space after passing through the mouth of the retrieval end,
        the retrieval end comprising a main body portion having a diameter of about 25-35 mm in the expanded state,
        the wire weave comprising 11-21 picks per centimeter, the wires of the wire weave having a diameter of about 100 to about 300 µm, and
        a lumen extending from a proximal end of the inner sheath to the retrieval end, the lumen housing a control line that is attached to the retrieval end at least at the mouth and is configured to change a position of the mouth of the retrieval end relative to the endovascular device within the subject's internal body space;
    wherein when at least a portion of the retrieval end of the inner sheath is withdrawn into the outer sheath following capture of the endovascular device within the interior space of the retrieval end, the retrieval end exerts an inward force that at least partially collapses or compresses the endovascular device.

2. The system according to claim 1, further comprising at least one manipulation tool for grips, grasps, grapples, ensnares, moves, captures, changes the orientation, or manipulates the endovascular device, the manipulation tool being deployable into the subject's internal body space via a lumen in the inner sheath.

3. The system according to claim 1, further comprising a suture line having a loop portion that is positioned around the circumference of the mouth of the retrieval end and that is used to transition the mouth between the opened state and the closed state.

4. The system according to claim 3 wherein said suture line transitions the mouth between the opened state and the closed state independently of whether the retrieval sheath has been at least partially withdrawn into the outer sheath.

5. The system according to claim 3, wherein the suture line is housed within a lumen in the inner sheath.

6. The system according to claim 1, wherein the control line also provides longitudinal support for the retrieval end while the object is being drawn into the retrieval end.

7. The system according to claim 1, wherein the wire weave has a first braiding angle when the retrieval end is in the expanded state and before withdrawal of any portion of the retrieval end into the outer sheath.

8. The system according to claim 7, wherein the retrieval end elongates and the braiding angle of said wire weave decreases from the first braiding angle to a second braiding angle in response to withdrawal of at least a portion of the retrieval end of the inner sheath into the outer sheath.

9. The system according to claim 1, wherein the control line is attached to the retrieval end at one or more additional locations on the retrieval end.

10. A method for percutaneously retrieving an endovascular device within a subject's internal body space comprising:
    delivering to the subject's internal body space an outer sheath having a lumen;

introducing an inner sheath into the lumen of the outer sheath, the inner sheath comprising a distal retrieval end comprising a wire weave formed from wires and having one or more compressed states and an expanded state, the retrieval end adopting one of the compressed states when the retrieval end is housed within the lumen of the outer sheath, and adopting the expanded state when the retrieval end is deployed into the subject's internal body space by exiting a distal end of the outer sheath, the retrieval end having a mouth through which the endovascular device can be passed into an interior space within the retrieval end when the retrieval end is in the expanded state, the mouth being adjustable between an opened state and a closed state so that the endovascular device can be enclosed within the interior space after passing through the mouth of the retrieval end, the retrieval end comprising a main body portion having a diameter of about 25-35 mm in the expanded state, the wire weave comprising 11-21 picks per centimeter, the wires of the wire weave having a diameter of about 100 to about 300 µm, and a lumen extending from a proximal end of the inner sheath to the retrieval end, the lumen housing a control line that is attached to the retrieval end at least at the mouth and is configured to change a position of the mouth of the retrieval end relative to the endovascular device within the subject's internal body space;

advancing the inner sheath through the lumen of the outer sheath until the retrieval end is deployed into the subject's internal body space by exiting the distal end of the outer sheath;

capturing the endovascular device at least partially within the interior space of the retrieval end;

at least partially closing the mouth of the retrieval end in order to enclose the endovascular device within the interior space of the retrieval end;

withdrawing the inner sheath through the lumen of the outer sheath until the retrieval end exerts an inward force that at least partially collapses or compresses the endovascular device; and, withdrawing the retrieval end into the lumen of the outer sheath, thereby removing the endovascular device from the subject's internal body space.

11. The method according to claim 10, wherein the inner sheath is introduced into the lumen of the outer sheath by introducing the inner sheath into the lumen of a loader tube via a proximal end of the loader tube;

advancing inner sheath through the lumen of the loader tube to a distal end thereof until the inner sheath exits the distal end of the loader tube and enters the lumen of the outer sheath via a proximal end of the outer sheath; and, advancing the inner sheath until the retrieval end thereof approaches, but does not exit, the distal end of the outer sheath.

12. The method according to claim 10, further comprising, following deployment of the retrieval end into the subject's internal body space, adjusting the position of the retrieval end relative to the endovascular device by use of the control line, wherein the control line is affixed to the retrieval end.

13. The method according to claim 12, comprising using the control line to position the retrieval end so that the endovascular device is proximate to the mouth of the retrieval end.

14. The method according to claim 10, further comprising, following deployment of the retrieval end into the subject's vasculature, advancing through a lumen of the inner sheath a manipulation tool that grips, grasps, grapples, ensnares, moves, captures, changes the orientation, or manipulates the object in order to assist in the step of capturing the endovascular device at least partially within the interior space of the retrieval end.

15. The method according to claim 14, further comprising adjusting a position of the retrieval end relative to the endovascular device by use of a control line, wherein the control line is affixed to the retrieval end, in order to place the mouth of the retrieval end proximate to the endovascular device at the same time that the manipulation tool grips, grasps, grapples, ensnares, moves, captures, changes the orientation, or manipulates the endovascular device.

16. The method according to claim 10, wherein the control line is attached to the retrieval end at one or more additional locations on the retrieval end.

17. A device for percutaneously retrieving an endovascular device from a subject's internal body space comprising:

an elongated tube portion that terminates in a distal retrieval end, the distal retrieval end comprising a wire weave formed from wires having a diameter of about 100 to about 300 µm and comprising 11-21 picks per centimeter, the retrieval end having one or more compressed states and an expanded state, the retrieval end comprising a main body portion having a diameter of about 25-35 mm in the expanded state, the retrieval end adopting one of the compressed states when the retrieval end is housed within the lumen of an outer sheath, and adopting the expanded state when the retrieval end is deployed into the subject's internal body space by exiting a distal end of the outer sheath, the retrieval end having a mouth through which the endovascular device can be passed into an interior space within the retrieval end when the retrieval end is in the expanded state, the mouth being adjustable between an opened state and a closed state so that the endovascular device can be enclosed within the interior space after passing through the mouth of the retrieval end, and the elongated tube portion comprising a lumen extending from a proximal end of the elongated tube portion to the retrieval end, the lumen housing a control line that is attached to the retrieval end at least at the mouth and is configured to change a position of the mouth of the retrieval end relative to the endovascular device within the subject's internal body space.

18. The device according to claim 17 further comprising a suture line having a loop portion that is positioned around the circumference of the mouth of the retrieval end and that is used to transition the mouth between the opened state and the closed state.

19. The device according to claim 18, wherein the suture line is housed within a lumen in the elongated tube portion.

20. The device according to claim 17, wherein the control line that is affixed to the retrieval end.

21. The device according to claim 17, wherein the control line also provides longitudinal support for the retrieval end while the endovascular device is being drawn into the retrieval end.

22. The device according to claim 17, wherein the elongated tube portion comprises two interior lumens.

23. The device according to claim 17, wherein the elongated tube portion comprises three interior lumens.

24. The device according to claim 17, wherein the mouth can be transitioned into the closed state independently of whether the retrieval end is being withdrawn into the outer sheath.

25. The device according to claim 17 wherein the wire weave of the retrieval end has a first braiding angle when the retrieval end is in the expanded state and before withdrawal of any portion of the retrieval end into the outer sheath.

26. The device according to claim 25, wherein the retrieval end elongates and the braiding angle of said wire weave decreases from the first braiding angle to a second braiding angle in response to withdrawal of at least a portion of the retrieval end into the outer sheath.

27. The device according to claim 17, wherein the control line is attached to the retrieval end at one or more additional locations on the retrieval end.

28. A device for percutaneously retrieving an endovascular device from a subject's internal body space comprising:
   an elongated tube for introduction into a subject that terminates in a retrieval end;
   the retrieval end comprising a wire weave formed from wires having a diameter of about 100 to about 300 μm and comprising 11-21 picks per centimeter,
   the retrieval end being expandable into an expanded state;
   the retrieval end comprising a main body portion having a diameter of about 25-35 mm in the expanded state;
   the retrieval end further having a mouth through which the endovascular device can be passed into a space within the retrieval end when the retrieval end is in the expanded state;
   the mouth being adjustable between an opened state and a substantially closed state so that the endovascular device can be retained within the retrieval end after passing through the mouth of the retrieval end; and,
   the elongated tube comprising a lumen extending from a proximal end of the elongated tube to the retrieval end, the lumen housing a control line that is attached to the retrieval end at least at the mouth and is configured to change a position of the mouth of the retrieval end relative to the endovascular device within the subject's internal body space.

29. The device according to claim 28, wherein the mouth can be transitioned into the substantially closed state independently of whether the retrieval end is being transitioned from the expanded state to an at least partially collapsed state.

30. The device according to claim 28, wherein the wire weave of the retrieval end has a first braiding angle when the retrieval end is in the expanded state.

31. The device according to claim 30, wherein the retrieval end elongates and the braiding angle of said wire weave decreases from the first braiding angle to a second braiding angle when the retrieval end is transitioned from the expanded state to an at least partially collapsed state.

32. The device according to claim 28, wherein the control line is attached to the retrieval end at one or more additional locations on the retrieval end.

\* \* \* \* \*